United States Patent [19]

Hawman

[11] Patent Number: 4,659,935
[45] Date of Patent: Apr. 21, 1987

[54] BILATERAL COLLIMATOR FOR ROTATIONAL CAMERA TRANSAXIAL SPECT IMAGING OF SMALL BODY ORGANS

[75] Inventor: Eric G. Hawman, Buffalo Grove, Ill.

[73] Assignee: Siemens Gammasonics, Inc., Des Plaines, Ill.

[21] Appl. No.: 703,789

[22] Filed: Feb. 21, 1985

[51] Int. Cl.$^4$ .............................................. G21K 1/02
[52] U.S. Cl. ............................. 250/505.1; 250/363 S; 378/149
[58] Field of Search .................... 250/363 SB, 363 SC, 250/505.1; 378/149

[56] References Cited

U.S. PATENT DOCUMENTS

| | | | |
|---|---|---|---|
| 4,181,839 | 1/1980 | Hatton | 250/505 |
| 4,197,460 | 4/1980 | Anger | 250/363 |
| 4,389,569 | 6/1983 | Hattori et al. | 250/363 SB |
| 4,419,763 | 12/1983 | Hawman | 378/149 |

OTHER PUBLICATIONS

*Journal of Nuclear Medicine*, vol. 18, No. 4 (1977).
*IEEE Transactions on Nuclear Science*, vol. NS-21, No. 3, (1974).
*IEEE Transactions on Nuclear Science*, vol. NS-27, No. 1, (1980).
Lasker et al., "Emission Computed Tomography: Versatile Limited Software", in Emission Computed Tomography: Current Trends, ed. by P. D. Esser (Society of Nuclear Medicine, N.Y., 1983).
*Journal of Nuclear Medicine*, vol. 23, No. 9 (1982) pp. 830-835, Chang et al, "A New Collimator for Cardiac Tomography: The Quadrant Slant-Hole Collimator".
*IEEE Transactions on Nuclear Science*, vol. NS-26, No. 1 (2/1979) pp. 610-618 Jaszczak et al., "Single Photon Emission Computed Tomography Using Multi-Slice Fan Beam Collimators".

*Primary Examiner*—Bruce C. Anderson
*Assistant Examiner*—Jack I. Berman
*Attorney, Agent, or Firm*—Mark H. Jay

[57] ABSTRACT

A bilateral collimator for rotational camera transaxial SPECT imaging of small body organs produces two different simultaneous views of a body organ to be imaged. The views are produced by groups of passageways which do not intersect each other.

9 Claims, 12 Drawing Figures

BILATERAL COLLIMATOR FOR ROTATIONAL CAMERA TRANSAXIAL SPECT IMAGING OF SMALL BODY ORGANS

BACKGROUND OF THE INVENTION

The invention relates to collimators, and more particularly relates to collimators used with imaging gamma cameras.

A conventional gamma camera has a relatively large (perhaps 15 inches in diameter) sensitive crystal surface. When a conventional non-focusing parallel-hole collimator is used to image relatively small organs such as the heart or brain, a large fraction of the available crystal surface remains unutilized. This is disadvantageous because a low utilization of sensitive crystal surface decreases sensitivity and resolution and also increases the time required for imaging.

It would therefore be advantageous to provide a device which would increase the utilization of the sensitive surface of a scintillation crystal when imaging relatively small organs such as the heart or brain.

One object of the invention is to increase the sensitivity and resolution of a gamma scintillation camera.

Another object is to increase gamma camera sensitivity and resolution when imaging small body organs, particularly the heart and brain.

Yet another object is to generally improve on known collimators for use with scintillation cameras.

SUMMARY OF THE INVENTION

In accordance with the invention, there is provided a bilateral collimator for rotational camera transaxial SPECT (single photon emission computed tomography) imaging of small body organs, which comprises a radiation-absorbing material having passageways through which radiation can pass. The passageways are divided into first and second groups which define respectively first and second views of a body organ to be imaged. None of the passageways in one group intersect any of the passageways in the other group.

The invention causes two entirely separated views of the imaged body organ to be projected onto the sensitive crystal surface. This increases the utilization of the sensitive crystal surface, increasing resolution and sensitivity and decreasing the time required for imaging. The images so projected are separately processed and back-projected into the same image space.

Crystal utilization can be further improved by choosing appropriate views of the body organ to be imaged. The choice of view characteristics is determined by the availability of computer resources and the maximum acceptable times permitted to reconstruct an image and to acquire patient image data.

The invention will be better understood with reference to the following drawings and the detailed description of preferred embodiments.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
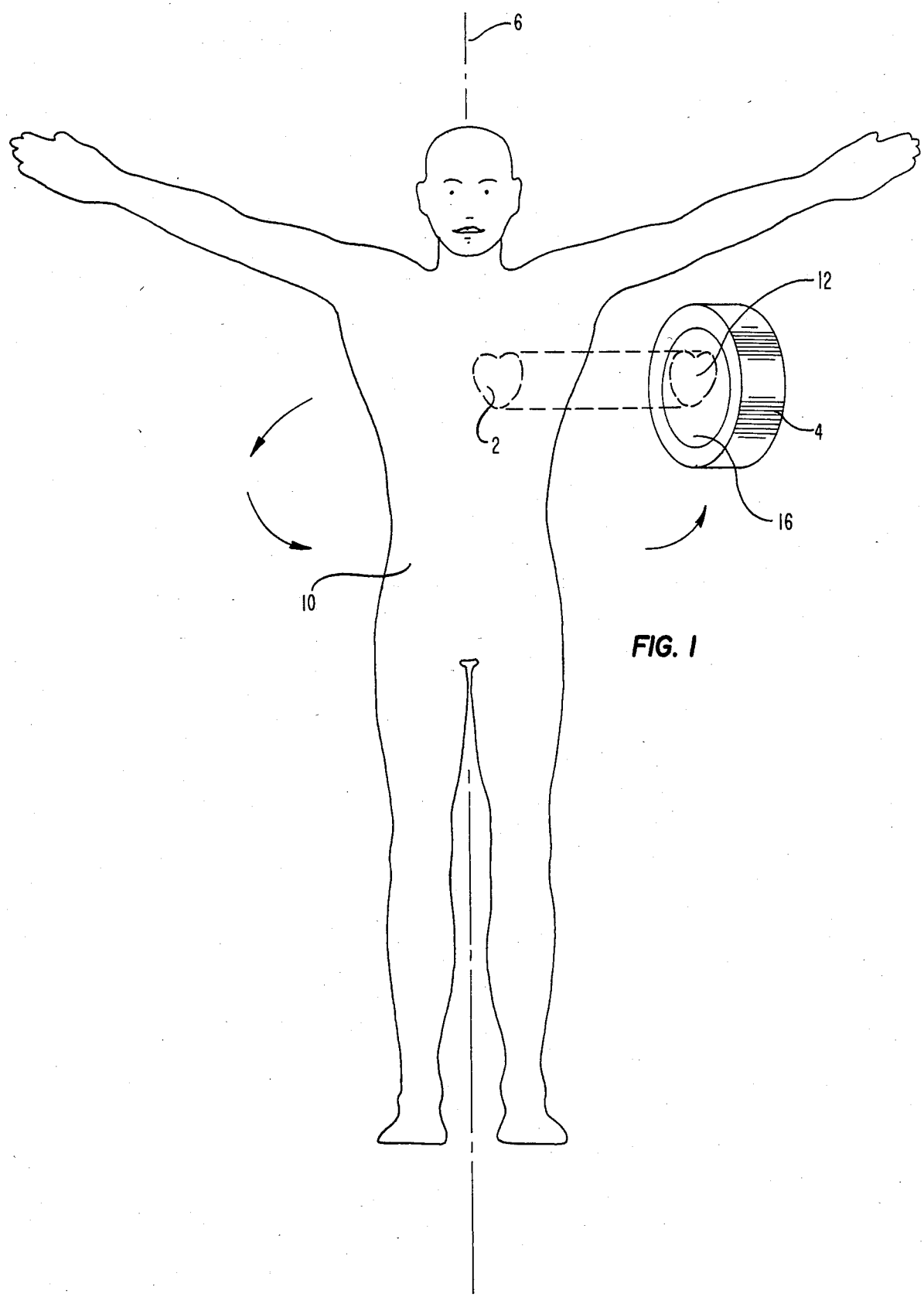
FIG. 1 schematically shows how a scintillation camera is rotated about a patient during a rotational camera transaxial SPECT examination of the heart.
Figure 2:
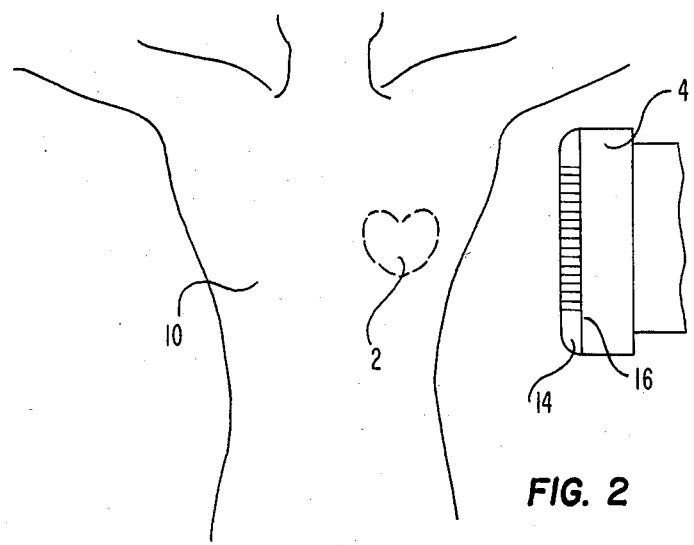
FIGS. 2 and 3 show how the sensitive surface of a scintillation camera with a conventional collimator is utilized when imaging a small body organ such as the heart.
Figure 3:
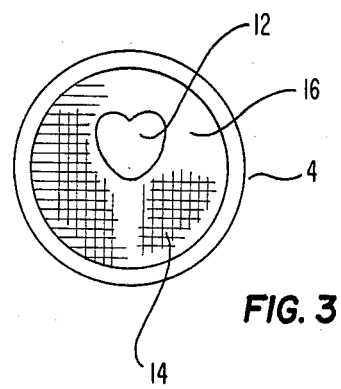

As shown in FIGS. 1 and 2, to form a conventional rotational camera transaxial SPECT image of a small body organ such as the heart 2, a gamma camera 4 is rotated about the axis 6 of the patient 10. Gamma radiation passing through or out of the patient 10 causes an image 12 to be projected through a collimator 14 onto the sensitive crystal surface 16 of the camera 4. As can be seen from FIGS. 2 and 3, the image 12 so projected occupies only a comparatively small fraction of the surface 16. This is because a conventional collimator 14 is of the parallel hole type, so that the image 12 is exactly the same size as the body organ 2 to be imaged. In effect, most of the surface 16 is wasted because no image is projected on it.

Figure 4:
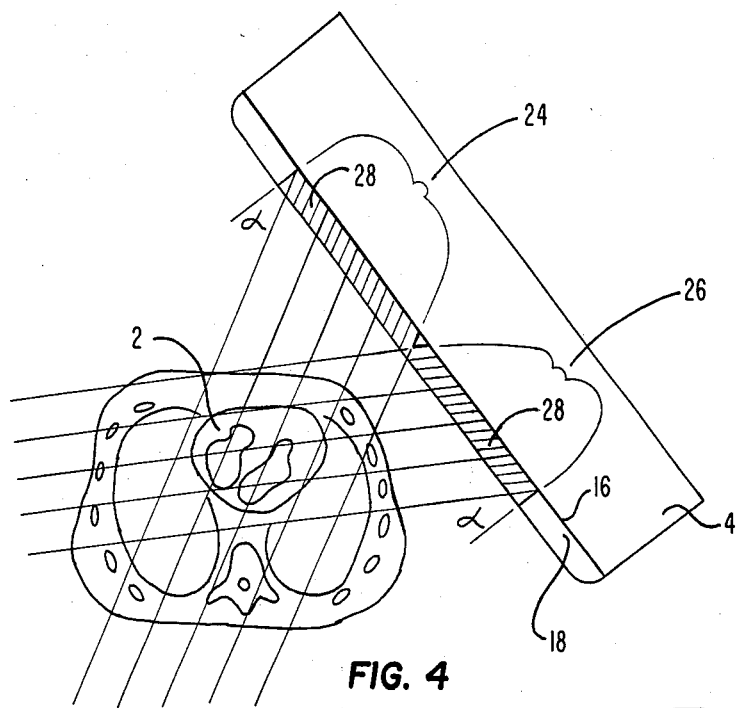
FIG. 4 shows a cross-sectional view of a first preferred embodiment used in imaging the heart.
Figure 5:
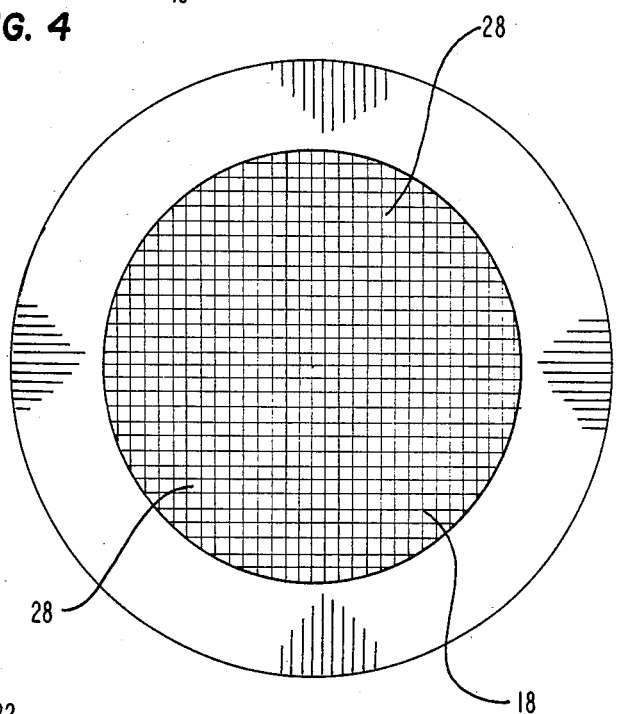
FIG. 5 shows a front view of the first preferred embodiment.
Figure 6:
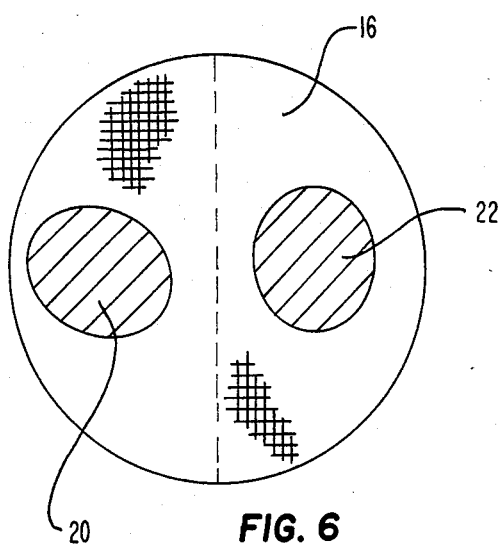
FIG. 6 illustrates the utilization of the sensitive crystal surface of the scintillation camera using the first preferred embodiment.

A first preferred embodiment of the invention is shown in FIGS. 4–6. Here, the collimator 18 is bilateral, i.e. it simultaneously produces two views 20 and 22 of the heart 2. (The heart 2 is used only as an example—another small body organ can be imaged instead). The views 20 and 22 are defined by the directions of a first group 24 and a second group 26 of passageways 28. Within each group 24, 26, all the passageways 28 are parallel. The collimator 18 is made of a radiation-absorbing material, lead being preferred. Only radiation which is parallel to a passageway 28 will reach the surface 16; obliquely directed radiation is absorbed by the collimator 18. In this embodiment the first and second groups 24 and 26 are mirror images of each other, so their constituent passageways 28 are symmetrical (i.e. they make equal angles α with a line normal to the surface 16 when the collimator 18 is mounted to the camera head 4). None of the passageways 28 in the first group 24 intersects any of the passageways 28 in the second group 26. Thus, the first and second views 20 and 22 do not overlap.

As shown in FIG. 6, each of the views 20 and 22 is slightly larger than the heart 2. This is because the sizes of the views 20 and 22 are equal to the size of the heart 2, divided by cos α. Since there are two views 20 and 22 of the heart 2 projected on the surface 16, the utilization of the surface 16 is further increased. As a result of this increased utilization of the surface 16, more information is collected during the same exposure time. This increases sensitivity and resolution, or alternatively makes it possible to produce an acceptable image with a shorter exposure time.

Figure 7:
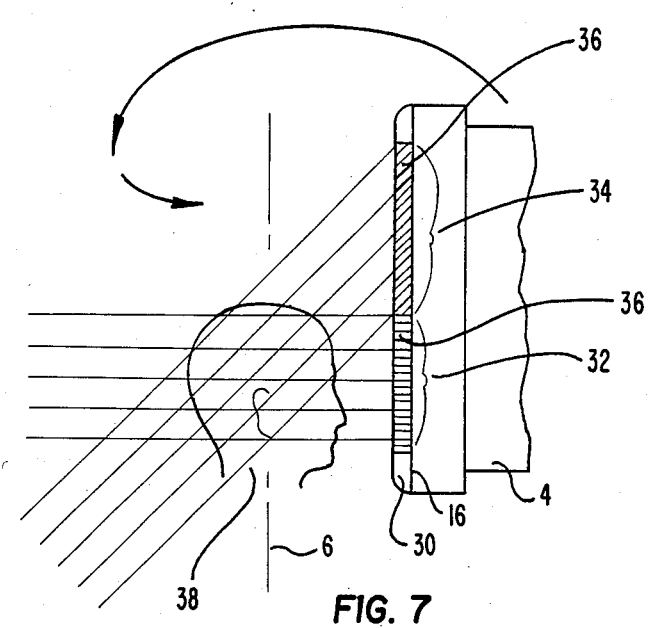
FIGS. 7 and 8 show side and top cross-sectional views respectively of a second preferred embodiment.
Figure 8:
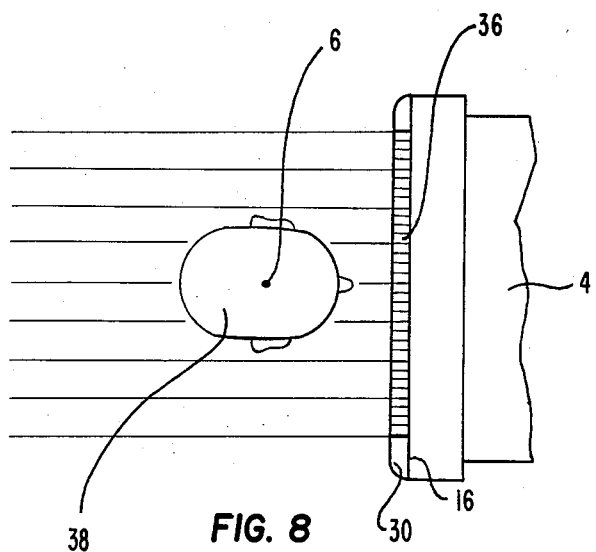
Figure 9:
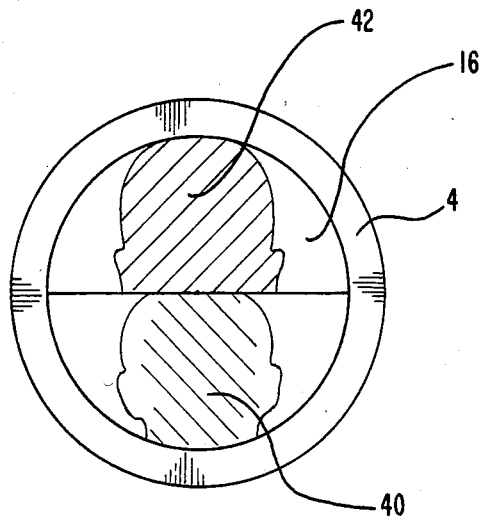
FIG. 9 illustrates the utilization of the sensitive crystal surface of the scintillation camera using the second preferred embodiment.

In a second preferred embodiment, (FIGS. 7-9) the collimator 30 also has two groups 32 and 34 of parallel passgeways 36, but the first and second groups 32 and 34 are not mirror images of each other. Here, the first group 32 of passageways 36, as viewed from the side, is normal to the axis 6 about which the camera 4 rotates.

The second group 34 of passageways 36 is, as so viewed, oblique to the axis 6. As viewed along the axis 6, all of the passageways 36 are perpendicular to the axis 6.

The second preferred embodiment is illustrated as imaging the head 38 (actually the brain, not specifically shown), but this is not required; other small body organs can also be imaged. In this second preferred embodiment, the first view 40 is actual size, while the second view 42 is not.

Figure 10:
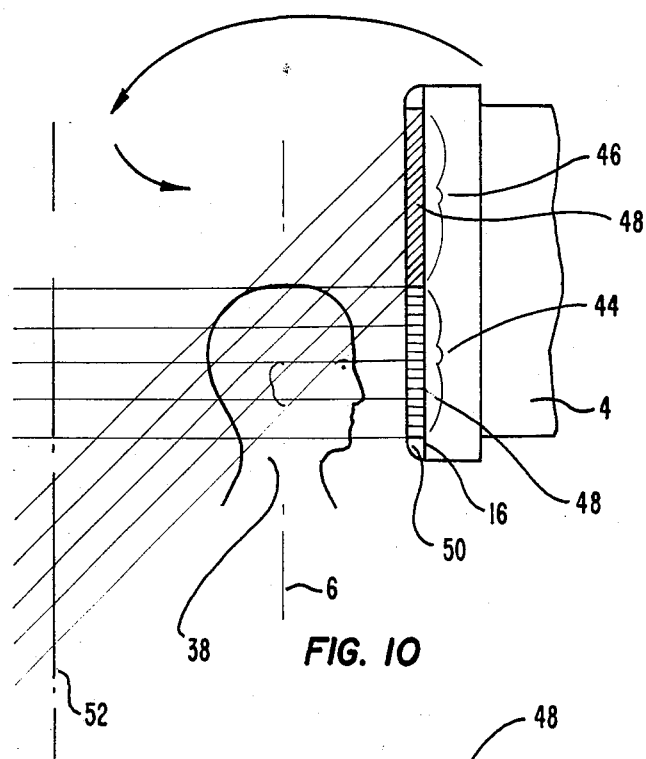
FIGS. 10 and 11 show side and top cross-sectional views respectively of a third preferred embodiment of the invention.
Figure 11:
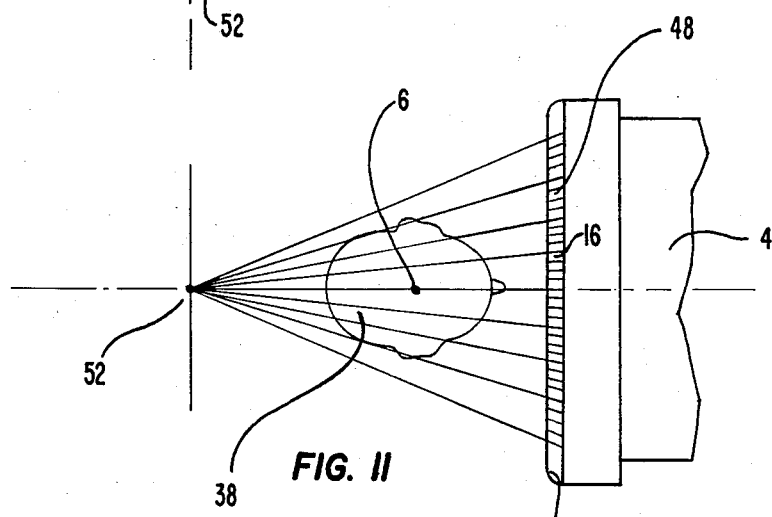
Figure 12:
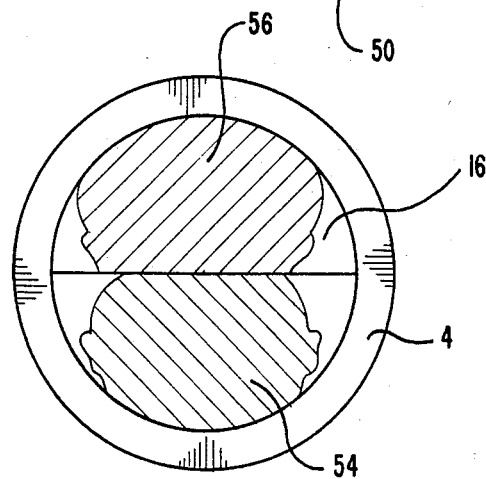
FIG. 12 shows the utilization of the sensitive crystal surface of the scintillation camera using the third preferred embodiment.

The third preferred embodiment (FIGS. 10-12) is likewise illustrated as imaging the head 38 (actually the brain) of a patient. Here, the first and second groups 44 and 46 of passageways 48 in the collimator 50 appear from the side to look identical to the groups 32 and 34 of passageways 36 in the collimator 30. However, as viewed along the axis 6, the groups 44 and 46 form a fan beam which is focussed along a focal line 52.

The resulting first and second views 54 and 56 are larger than the corresponding first and second views 40 and 46. This further increases utilization of the surface 16, further increasing sensitivity and resolution.

For clarity of illustration, the size of the passageways in the various embodiments has been exaggerated. Additionally, the illustrations are merely illustrative, and the dimensions and angles shown are not to scale.

The selection of the embodiment to be used (and of the particular orientations of the groups of passageways) depends upon the size of the organ to be imaged, the availability of computer resources, and the maximum acceptable times for data acquisition and production of a reconstructed image. This is because the more complicated the relationship between an undistorted image of a body organ under investigation and the view of that organ as it appears on the surface of the crystal, the more computer processing is required to create a reconstructed image. Thus, while, e.g. the third preferred embodiment utilizes a large fraction of the sensitive crystal surface of the camera and thus increases sensitivity and resolution, it takes more effective computer power to produce a reconstructed three-dimensional image.

The end product of the invention is the simultaneous acquisition of two different views of the body organ to be imaged. Preferably, each of the views is then separately filtered and processed and is then backprojected into the same image space in the computer to generate a fully reconstructed three-dimensional image.

Those skilled in the art will understand that changes can be made in the preferred embodiments here described, and that these embodiments can be used for other purposes. Such changes and uses are within the scope of the invention, which is limited only by the claims which follow.

What is claimed is:
1. In combination:
   a rotational camera transaxial SPECT camera; and
   a bilateral collimator, comprising a radiation-absorbing material having passageways through which radiation can pass, said passageways being divided into first and second groups and defining respectively first and second views of a body organ to be imaged.
2. The combination of claim 1, wherein all passageways in a one of said groups are nonintersecting with all passageways in another of said groups.
3. The combination of claim 1, wherein all the passageways in the first group are parallel to each other and all the passageways in the second group are parallel to each other.
4. The combination of claim 3, wherein the first and second views are symmetrical and the first and second groups are mirror images of each other.
5. The combination of claim 3, wherein the first and second views are perpendicular to an axis of rotation of the camera.
6. The combination of claim 2, wherein, as viewed perpendicular to an axis of rotation of the camera, one of said views appears perpendicular to said axis and another one of said views appears oblique thereto.
7. The combination of claim 6, wherein, as viewed along said axis, both of said views appear perpendicular to said axis.
8. The combination of claim 6, wherein, as viewed along said axis, both of said views appear fan-shaped.
9. The combination of claim 8, wherein both of said views focus along a common line.

* * * * *